(12) United States Patent
Asmus et al.

(10) Patent No.: US 7,316,148 B2
(45) Date of Patent: Jan. 8, 2008

(54) PROTECTIVE SHEET LOADER

(75) Inventors: Bruce Asmus, Minnetonka, MN (US);
Dennis Aamoth, Fridley, MN (US);
Thomas Walch, Centerville, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 347 days.

(21) Appl. No.: 11/058,391

(22) Filed: Feb. 15, 2005

(65) Prior Publication Data

US 2006/0183383 A1 Aug. 17, 2006

(51) Int. Cl.
*B21D 39/04* (2006.01)
*A61F 2/06* (2006.01)

(52) U.S. Cl. ............................ 72/402; 29/282; 29/283.5

(58) Field of Classification Search ............... 72/402; 29/237, 282, 283.5; 53/453, 559; 623/1.11
See application file for complete search history.

(56) References Cited

U.S. PATENT DOCUMENTS

| | | | |
|---|---|---|---|
| 4,240,241 A * | 12/1980 | Sanborn, Jr. .................. | 53/412 |
| 4,277,931 A * | 7/1981 | Mahaffy et al. ............... | 53/412 |
| 4,684,025 A * | 8/1987 | Copland et al. ............. | 206/484 |
| 4,905,450 A * | 3/1990 | Hansen et al. ................. | 53/410 |
| 5,437,083 A | 8/1995 | Williams et al. .............. | 29/235 |
| 5,546,646 A | 8/1996 | Williams et al. .......... | 29/407.08 |
| 5,672,169 A | 9/1997 | Verbeek .......................... | 606/1 |
| 5,725,519 A | 3/1998 | Penner et al. .................... | 606/1 |
| 5,738,674 A | 4/1998 | Williams et al. ............... | 606/1 |
| 5,746,764 A | 5/1998 | Green et al. .................. | 606/194 |
| 5,810,873 A | 9/1998 | Morales ........................ | 606/198 |
| 5,836,952 A | 11/1998 | Davis et al. ................. | 606/108 |
| 5,944,735 A | 8/1999 | Green et al. ................. | 606/194 |
| 5,947,993 A | 9/1999 | Morales ....................... | 606/198 |
| 5,976,181 A | 11/1999 | Whelan et al. ................. | 623/1 |
| 6,024,737 A | 2/2000 | Morales ......................... | 606/1 |
| 6,096,027 A | 8/2000 | Layne ............................ | 606/1 |
| 6,141,855 A | 11/2000 | Morales ....................... | 29/516 |
| 6,352,547 B1 | 3/2002 | Brown et al. ............... | 606/198 |

(Continued)

FOREIGN PATENT DOCUMENTS

EP 0 826 346 A1 8/1997

(Continued)

OTHER PUBLICATIONS

U.S. Appl. No. 10/826,035, filed Apr. 16, 2004, Perreault.

(Continued)

*Primary Examiner*—Daniel C Crane
(74) *Attorney, Agent, or Firm*—Vidas, Arrett & Steinkraus, P.A.

(57) ABSTRACT

A protective sheet loader may comprise a first roller, a second roller, a sheet of material spanning between the first and second rollers, and a loading mechanism. A portion of the sheet of material may be loaded into the crimping chamber of an apparatus for reducing the size of a medical device. A medical device may be placed within the crimping chamber such that the sheet of material forms a barrier between the walls of the crimping chamber and the medical device and prevents cross-contamination between the medical device and the crimping device. After a crimping step is completed, the medical device and the contaminated portion of the sheet of material may be removed from the crimping chamber, and a clean portion of the sheet of material may be loaded into the crimping chamber.

24 Claims, 11 Drawing Sheets

U.S. PATENT DOCUMENTS

| | | | |
|---|---|---|---|
| 6,360,577 B2 | 3/2002 | Austin | 72/402 |
| 6,629,350 B2 | 10/2003 | Motsenbocker | 29/283.5 |
| 6,726,713 B2 * | 4/2004 | Schaldach et al. | 623/1.11 |
| 6,859,986 B2 * | 3/2005 | Jackson et al. | 29/458 |
| 7,013,622 B2 * | 3/2006 | Berdelle-Hilge | 53/451 |
| 2002/0116045 A1 | 8/2002 | Eidenschink | 623/1.11 |
| 2003/0055482 A1 | 3/2003 | Schwager et al. | 632/1.11 |
| 2003/0192164 A1 | 10/2003 | Austin | 250/306 |
| 2004/0199239 A1 | 10/2004 | Austin et al. | 623/1.11 |
| 2005/0033404 A1 | 2/2005 | Eidenschink | 623/1.11 |
| 2005/0188525 A1 | 9/2005 | Eidenschink | 29/508 |

OTHER PUBLICATIONS

U.S. Appl. No. 10/788,088, filed Feb. 26, 2004, Weber et al.
U.S. Appl. No. 10/826,196, filed Apr. 16, 2004, Eden.

* cited by examiner

PROTECTIVE SHEET LOADER

BACKGROUND OF THE INVENTION

Stents, stent delivery assemblies and other expandable medical devices are utilized in a number of medical procedures and situations, and as such their structure and function are well known. A stent is a generally cylindrical prosthesis introduced via a catheter into a lumen of a body vessel in a configuration having a generally reduced diameter and then expanded to the diameter of the vessel. In its expanded configuration, the stent supports and reinforces the vessel walls while maintaining the vessel in an open, unobstructed condition.

Stents are available in both self-expanding and inflation expandable configurations. Inflation expandable stents are well known and widely available in a variety of designs and configurations. Both self-expanding and inflation expandable stents may be crimped to their reduced configuration after being disposed about a delivery catheter. They are maneuvered to the deployment site and expanded to the vessel diameter either by fluid inflation of a balloon positioned between the stent and the delivery catheter, or upon release of the self-expanding stent from its crimped state, for example by retraction of a retaining sleeve.

Stents may be crimped or reduced in size by a suitable crimping device, for example as disclosed in U.S. patent application Ser. Nos. 10/826,196; 10/788,088; 10/826,035; and US20030192164A1; and U.S. Pat. Nos. 6,629,350; and 6,360,577, the entire disclosures of which are incorporated herein in their entireties.

When a stent includes a coating, such as a polymer or a drug coating, it may be possible for a crimping device to undesirably affect the coating during crimping. Further, crimping devices may require cleaning after a crimping step as coating material residuals may be left in the crimping device.

There remains a need for a system and method of crimping a stent or other expandable medical device which provides added protection to the device being reduced in size. There remains a need for a system and method of crimping a stent or other expandable medical device which prevents contamination of the contacting surfaces of the crimping device.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

In some embodiments, the present invention comprises a sheet loader which may be used in conjunction with a crimping device for reducing the size of a medical device. The sheet loader may load a portion of a protective sheet into the crimping chamber of the crimping device. A medical device may be placed within the crimping chamber such that the protective sheet forms a barrier between the walls of the crimping chamber and the medical device. The size of the crimping chamber may be reduced, thereby reducing the size of the medical device. Desirably, the protective sheet may be kept under tension during the crimping step, and any excess portion of the protective sheet may be removed from the crimping chamber as the size is reduced. Desirably, the protective sheet may prevent cross-contamination between the crimping device and the medical device. Once a crimping step is completed, the crimped medical device and the portion of the protective sheet which has been used may be removed from the crimping chamber, a clean portion of the protective sheet may be loaded into the crimping chamber and another crimping step may be performed.

In one embodiment, an apparatus for reducing the size of a medical device may comprise a plurality of moveable blades arranged to form a chamber, the size of the chamber being adjustable. A sheet of protective material may span between a first roller and a second roller, and a loading mechanism may be arranged to load a portion of the sheet of protective material into the chamber.

In another embodiment, a protective sheet loader for use with a stent crimper may comprise a supply roller, a discard roller, a sheet of material spanning between the supply roller and the discard roller and a loading mechanism. The loading mechanism may be constructed and arranged to load a portion of the sheet of material into the crimping chamber of a stent crimper.

In one embodiment, a method of reducing the size of an article may comprise providing a device for reducing the size of an article, the device having a chamber, the size of the chamber being adjustable. A sheet of material may be provided and a first portion of the sheet of material may be disposed within the chamber. An article may be provided and disposed within the chamber such that the first portion of the sheet of material within the chamber is oriented about the article. The size of the chamber may be reduced to reduce the size of the article.

These and other embodiments which characterize the invention are pointed out with particularity in the claims annexed hereto and forming a part hereof. However, for a better understanding of the invention, its advantages and objectives obtained by its use, reference should be made to the drawings which form a further part hereof and the accompanying descriptive matter, in which there are illustrated and described various embodiments of the invention.

BRIEF DESCRIPTION OF THE DRAWINGS

A detailed description of the invention is hereafter described with specific reference being made to the drawings.

DETAILED DESCRIPTION OF THE INVENTION

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Figure 1:
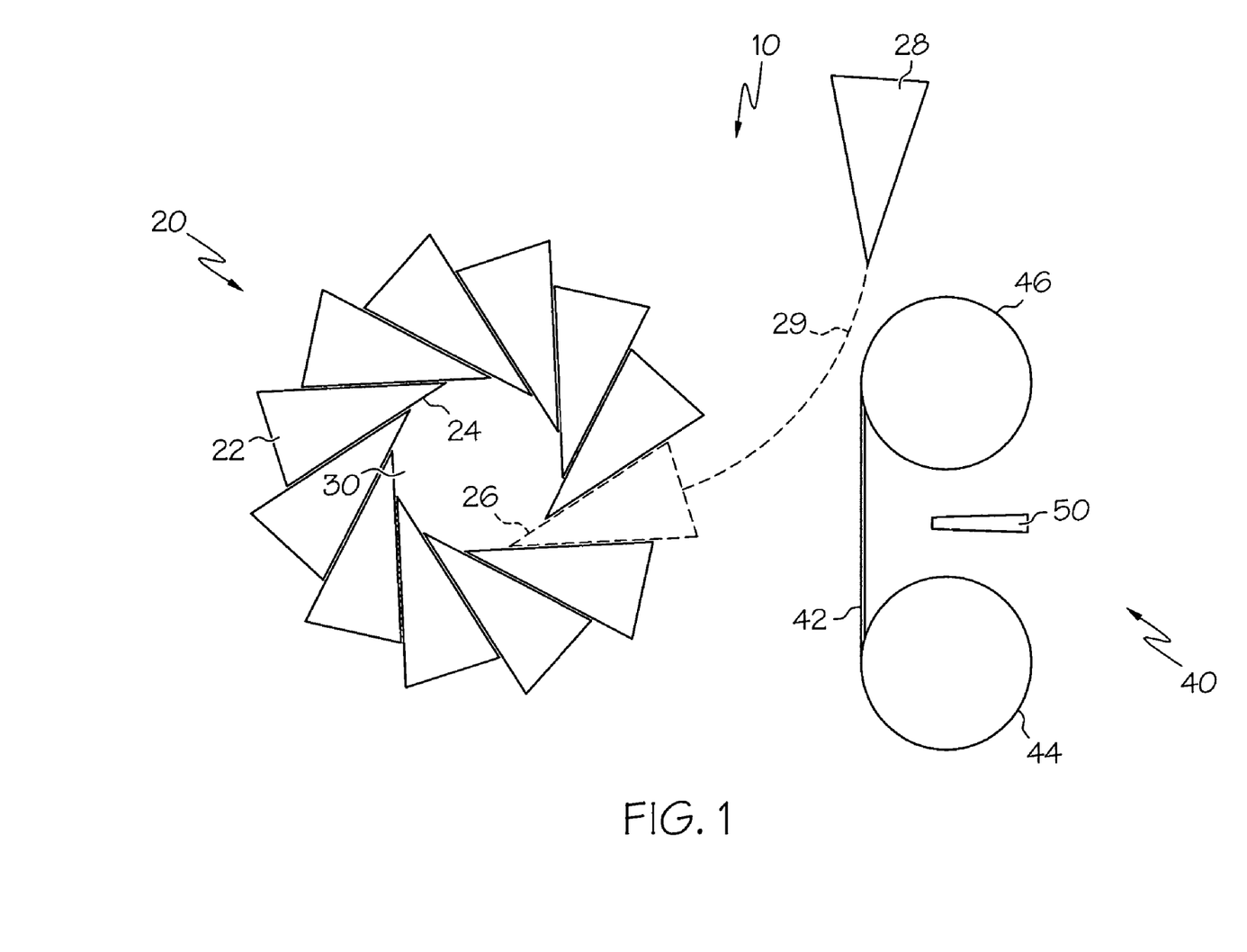
FIG. 1 shows an embodiment of a crimping apparatus having a protective sheet loader.

FIG. 1 shows an embodiment of a crimping apparatus 10 for reducing the size of a medical device. The apparatus 10 may include a crimping section 20 and a protective sheet loader section 40.

The crimping section 20 may comprise a plurality of segments or blades 22 arranged to form a chamber 30 of adjustable size. Each blade 22 may include a contacting surface 24 which may contact and apply inward forces to an article within the chamber 30. Desirably, the crimping section 20 may be suitable for reducing the size of a medical device. The crimping section 20 may function according to the principles disclosed in U.S. Pat. No. 6,629,350 and U.S. Pat. No. 6,360,577; U.S. patent application Ser. No. 10/788,088; or according to any other suitable stent crimping device.

The sheet loader section 40 may comprise a protective sheet 42 of material disposed between a first or supply roller 44 and a second or discard roller 46. The sheet loader section 40 may further include a loading mechanism 50 arranged to load a portion of the protective sheet 42 into the chamber 30.

Desirably, during operation of the apparatus 10 which will be described with respect to FIGS. 2-6, a portion of the protective sheet 42 may be oriented within the chamber 30 such that the sheet 42 abuts the inner periphery of the chamber 30. A medical device, such as a stent, may be oriented within the chamber 30 such that the sheet 42 forms a barrier between the medical device and the contacting surfaces 24 of the blades 22. The sheet 42 may be kept under tension as the size of the chamber 30 is reduced. When the size of the medical device has been suitably reduced, the medical device may be removed from the chamber 30, and the sheet 42 may be indexed such that the portion of the sheet within the chamber 30 is removed and a different portion of the sheet 42 may be loaded into the chamber 30.

The protective sheet 42 may comprise any compliant material suitable for forming a barrier between the blades 22 and the medical device being reduced in size. Desirably, the material used to form the sheet 42 may have a low coefficient of friction, for example 0.25 or less, or more desirably 0.1 or less. In some embodiments, the sheet 42 may comprise a polymer such as Mylar, nylon, Pebax, high density polyethylene, polytetrafluoroethylene (PTFE), etc.

The protective sheet 42 desirably functions to prevent cross-contamination between the blades 22 and a medical device being reduced in size. For example, when a medical device includes a coating, such as a lubricant or a drug, the sheet 42 prevents the coating from contaminating the blades 22. The sheet 42 may also function to prevent any contaminants present on the blades 22 from contaminating the medical device. Because the sheet 42 may prevent direct contact between the blades 22 and the medical device, in some embodiments the blades 22 may be made of a harder or longer lasting material than the blades of conventional stent crimpers, such as stainless steel or other metals.

In some embodiments, the protective sheet 42 may act as a cushion between the blades 22 and a medical device being reduced in size. The sheet 42 may help to prevent localized areas of high stress upon the medical device by distributing forces applied by the blades 22. Further, when the sheet 42 is placed under tension during a crimping step, uniform inward forces applied to the medical device by the sheet 42 may aid in providing a uniform reduced size to the medical device.

In some embodiments, the protective sheet 42 may help to prevent any gaps between the crimper blades 22 from catching any portions of the medical device during a crimping step or while removing the medical device from the crimping chamber after a crimping step.

In some embodiments, a lubricious coating may be applied to one or both sides of the sheet 42 to help prevent the sheet 42 from sticking to any other part of the apparatus 10.

The crimping section 20 may be provided with a gap 26 through which the sheet 42 may be loaded into the chamber 30. A gap 26 may be any suitable size which allows the sheet 42 to be loaded. In some embodiments, a gap 26 may be as small as possible. In some embodiments, the crimping section 20 may include a removable blade 28 which may be temporarily moved from its crimping position in order to form a gap 26. A removable blade 28 may be removed by any suitable movement mechanism 29, such as an electromagnet, an actuator, a spring, a motor, a pneumatic cylinder or device, etc.

Figure 2:
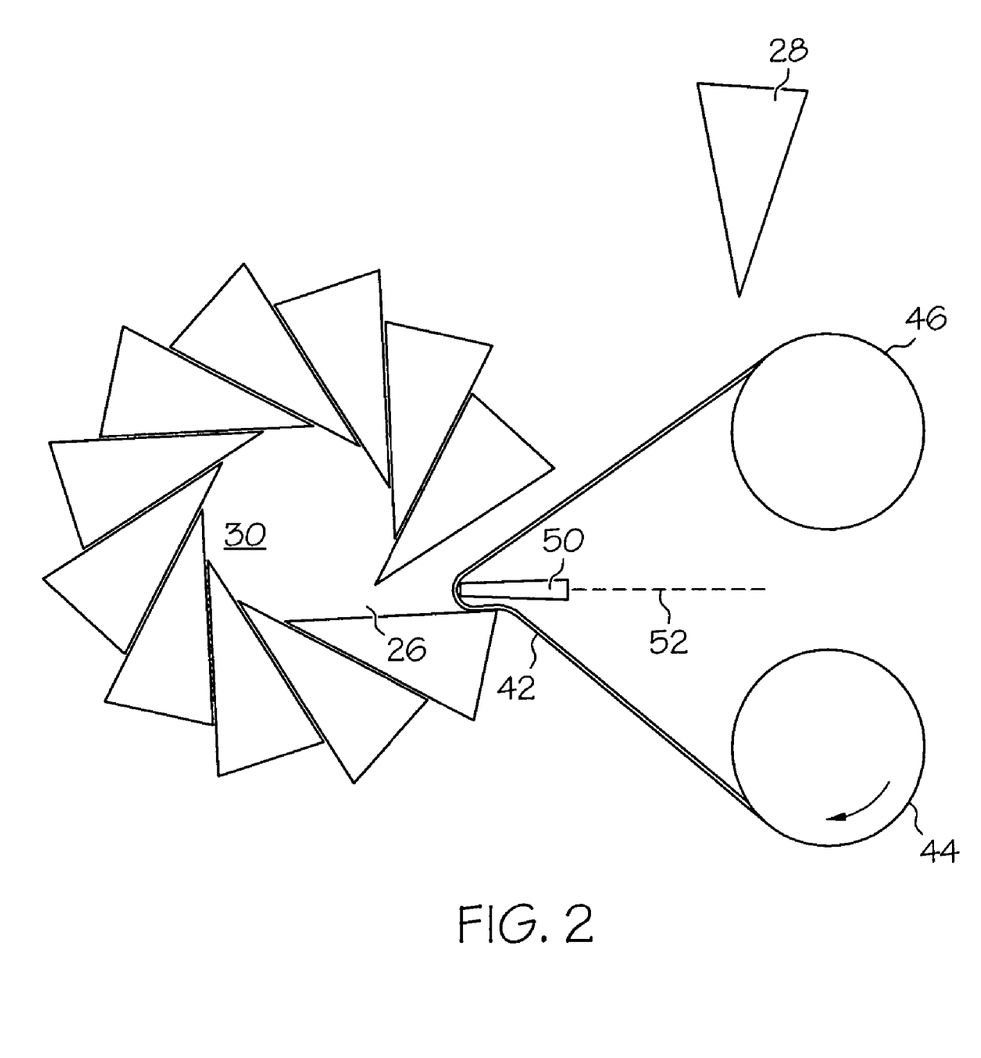
FIG. 2 shows a view of an embodiment of the invention where a protective sheet is being loaded into the crimping chamber.

FIG. 2 shows a removable blade 28 in a temporarily removed position in order to form a gap 26. In some embodiments, the loading mechanism 50 may be actuated along a track 52 in a direction toward the chamber 30 and may push a portion of the sheet 42 toward the chamber 30. Desirably, as the sheet 42 moves closer to the chamber 30, the supply roller 44 may rotate and provide an appropriate supply of the sheet 42. Desirably, the discard roller 46 may remain fixed against rotation.

Figure 3:
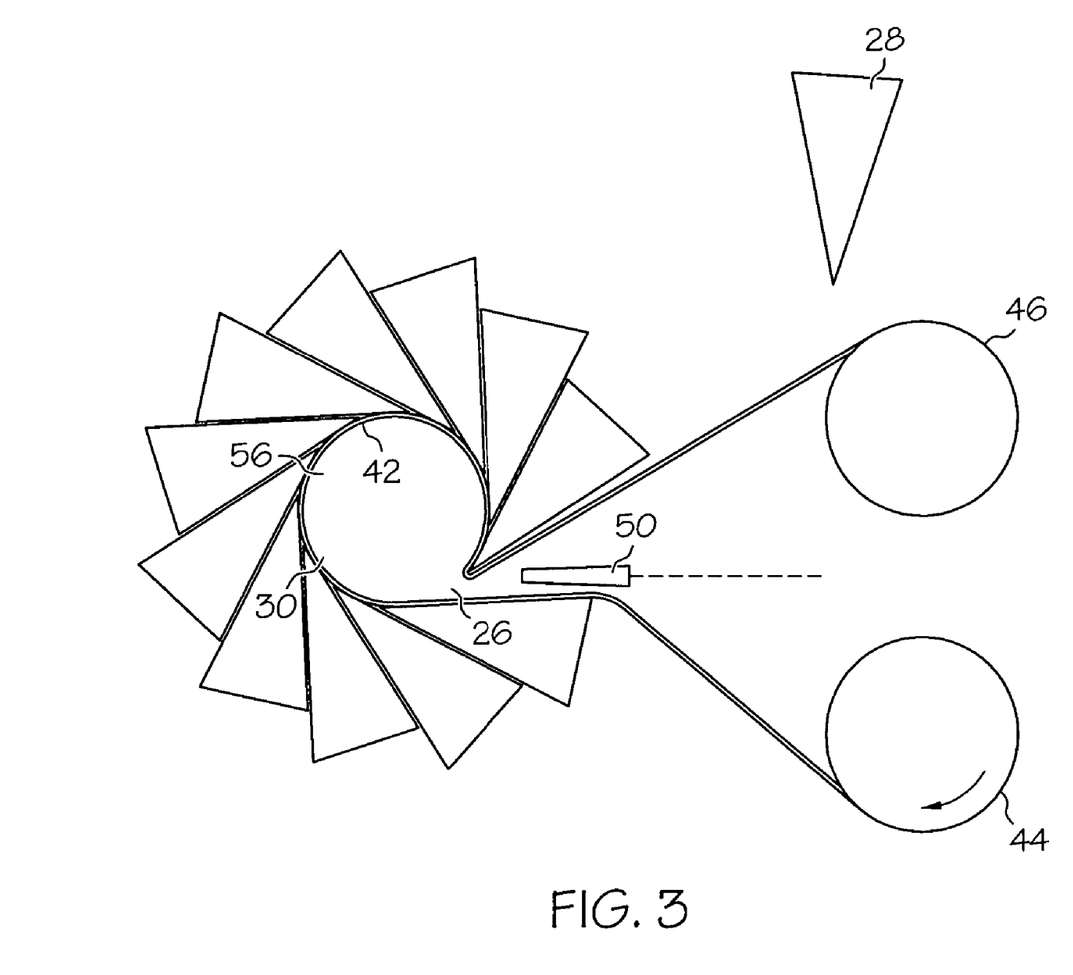
FIG. 3 shows a view of an embodiment of the invention where a protective sheet has been loaded into the crimping chamber.

Referring to FIG. 3, as the sheet 42 approaches the gap 26, the loading mechanism 50 may load a portion of the sheet 42 into the chamber 30. In some embodiments, the loading mechanism 50 may include a source for providing a stream of gas, such as an air jet or another suitable fluid directing mechanism, which may direct a stream of air, gas or another suitable fluid into the chamber 30. For example, the loading mechanism 50 may direct a pressurized air or gas stream against the sheet 42. The air stream may force a portion of the sheet 42 through the gap 26 and into the chamber 30. Desirably, the loading mechanism 50 may force enough of the sheet 42 into the chamber 30 that the sheet 42 may form and define an internal cavity 56 within the chamber 30. In some embodiments, the air stream may force the sheet 42 to abut the inner periphery of the chamber 30, and thus the volume of the cavity 56 defined by the sheet 42 may be substantially similar to the volume of the chamber 30. It may be desirable to control the amount of the sheet 42 entering the chamber 30 and/or the tension of the sheet 42 during loading by controlling the rotation of the supply roller 44 and/or the discard roller 46.

In addition to air, other suitable fluids which may be used by the loading system 50 include but are not limited to inert and relatively inert gases. Inert and relatively inert gases include but are not limited to nitrogen, helium, argon and combinations thereof.

At least a portion of a loading mechanism 50 may have a thin profile, which may allow at least a portion of the loading mechanism 50 to travel between crimper blades 22. Desirably, a portion of the loading mechanism 50 may approach the gap 26 and move as close to the gap 26 as possible.

Figure 4:
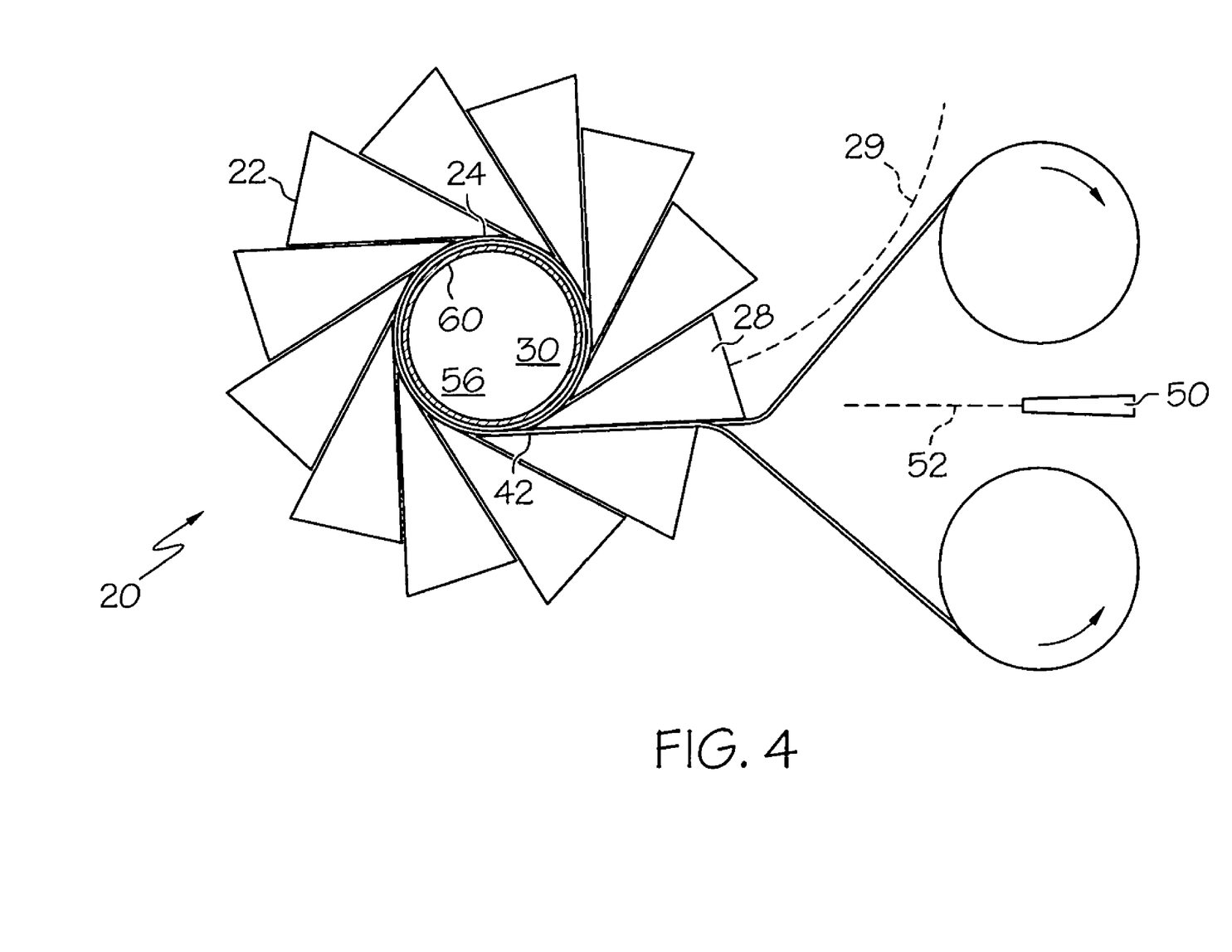
FIG. 4 shows a view of an embodiment of the invention where a protective sheet has been loaded into the crimping chamber and a medical device has been placed within the crimping chamber.

FIG. 4 shows a medical device 60, such as a stent, loaded within the cavity 56. Desirably, the medical device 60 is loaded into the cavity 56 such that the portion of the sheet 42 within the chamber 30 forms a barrier between the medical device 60 and the contacting surfaces 24 of the crimper blades 22. In some embodiments, the medical device 60 may be loaded into the cavity 56 while the loading mechanism 50 continues to provide an air stream which may hold the cavity 56 open.

In some embodiments, a medical device 60 may comprise a self-expanding stent. In some embodiments, a delivery catheter may be oriented within a self-expanding stent within the chamber 30. In some embodiments, a medical device 60 may comprise a balloon expandable stent, and a balloon catheter may be provided having an inflation balloon oriented within the balloon expandable stent within the chamber 30.

In some embodiments a medical device 60 may comprise one or more therapeutic agents. In some embodiments the agent may be placed on the medical device 60 in the form of a coating. In at least one embodiment the coating may include at least one therapeutic agent and at least one polymer agent.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate.

The loading mechanism 50 may be retracted and returned to its original position. In some embodiments the loading 50 mechanism may actuate away from the crimping section 20 along its track 52. The removable blade 28 may also be moved from the temporarily removed position to a crimping position as shown in FIG. 4.

Prior to a crimping step, the sheet 42 may be placed in tension, thereby removing any excess portions of the sheet 42 from the chamber 30 and causing the sheet 42 to continuously abut the outer periphery of the medical device 60. The sheet 42 may be placed in tension by the rotation of one or both of the rollers 44, 46 in the appropriate direction(s). In some embodiments, the supply roller 44 may remain fixed against rotation while the discard roller 46 rotates in a sheet removal direction. In some embodiments, the discard roller 46 may remain fixed against rotation while the supply roller 44 rotates in a sheet removal direction. In some embodiments, both the supply roller 44 and the discard roller 46 may rotate in the appropriate respective directions to place the sheet 42 under tension.

Figure 5:
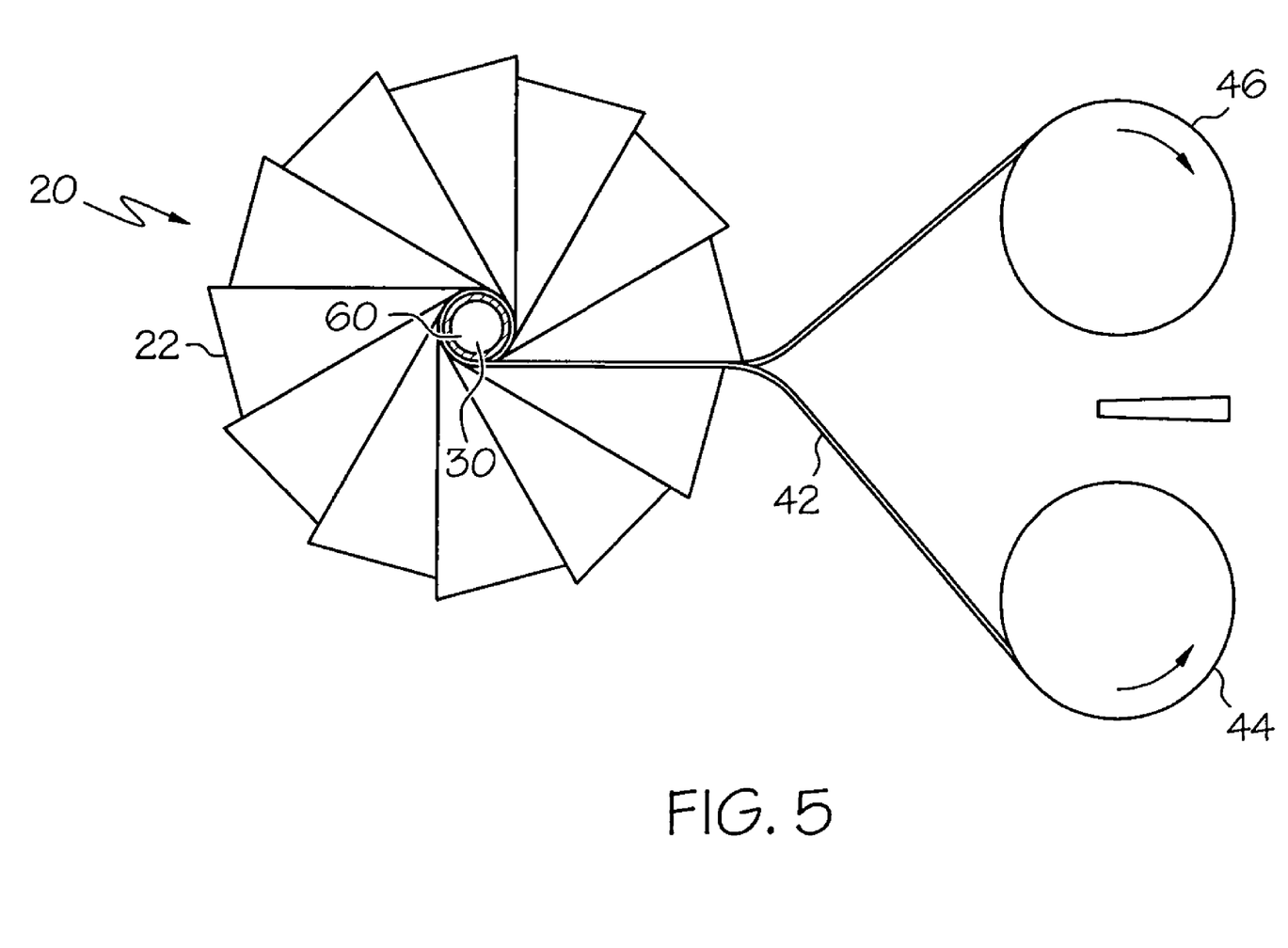
FIG. 5 shows a view of an embodiment of the invention during a crimping step.

As shown in FIG. 5, the crimping section 20 may perform a crimping step wherein the size of the chamber 30 is reduced, thereby reducing the size of the medical device 60 within the chamber. The sheet 42 may function to prevent cross-contamination between the blades 22 and the medical device 60 being reduced in size. The sheet 42 may further help to prevent damage to any coatings present on the medical device 60. Desirably, during the crimping step, the sheet 42 may be kept under tension. Desirably, as the size of the medical device 60 is reduced, any excess portion of the sheet 42 may be removed from the chamber 30 due to rotation of one or both of the rollers 44, 46. Thus, as the size of the medical device 60 is reduced, a portion of the sheet 42 will continue to wrap continuously about the outer periphery of the medical device 60 without wrinkling or bunching. After the crimping step, the medical device 60 may be removed from the chamber 30.

Figure 6:
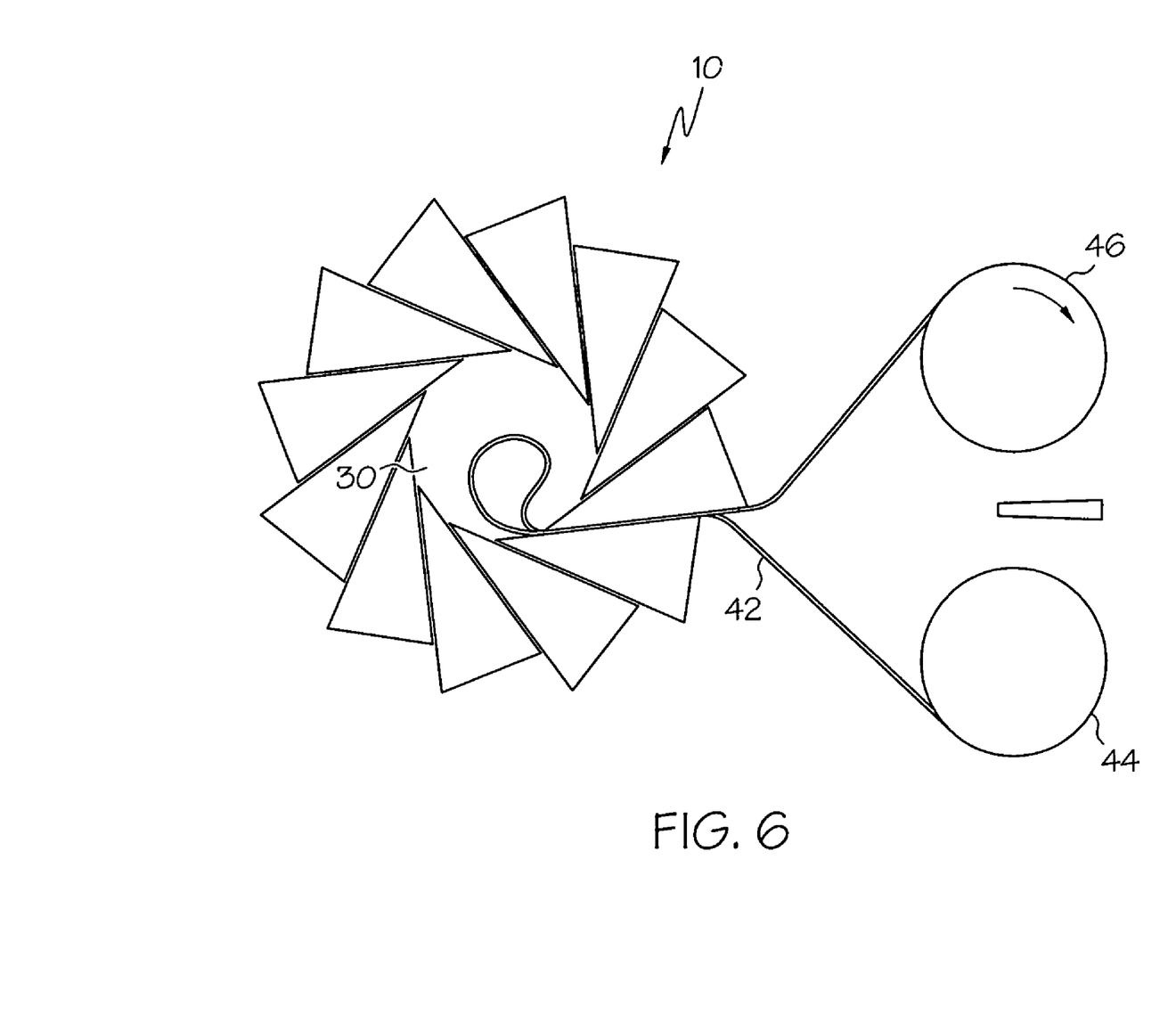
FIG. 6 shows a view of an embodiment of the invention after a crimping step, wherein a portion of the protective sheet is being removed from the crimping chamber.

FIG. 6 shows the apparatus 10 after the medical device 60 has been removed from the chamber 30. The size of the chamber 30 may be increased and the portion of the sheet 42 within the chamber 30 may be removed. Desirably, the discard roller 46 may rotate to remove all contaminated portions of the sheet 42. Once the contaminated portion of the sheet 42 has been removed, another portion of the sheet 42 may be loaded into the chamber 30 and another crimping operation may be conducted.

In some embodiments, at least one blade 22 of a crimping apparatus 10 may include multiple portions, wherein a portion of the blade is separately moveable with respect to another portion of the blade.

Figure 7:
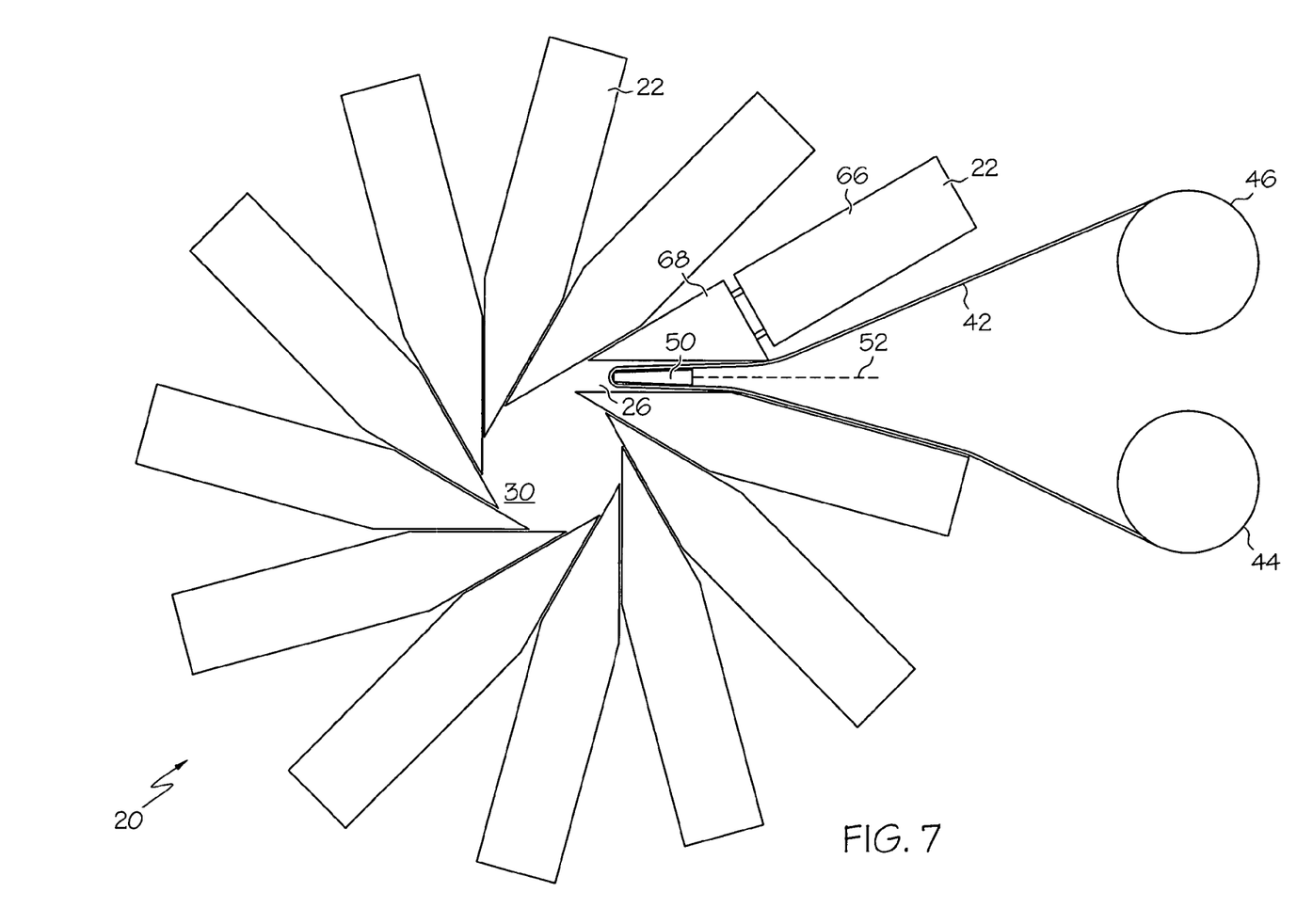
FIG. 7 shows another embodiment of the invention.

FIG. 7 shows an embodiment of a crimping apparatus 10 wherein the crimping section 20 includes a blade 22 having a body section 66 and a tip 68. The body section 66 may be attached to the crimping section actuation mechanism which controls movement of all of the blades 22 for crimping of a medical device. The tip 68 may be moveable separately from other portions of the apparatus 10 and may move between a crimping position and a temporarily removed position. FIG. 7 depicts the tip in a temporarily removed position, wherein a gap 26 is desirably present. The loading mechanism 50 may load a portion of the sheet 42 through the gap 26 and into the chamber 30.

Figure 8:
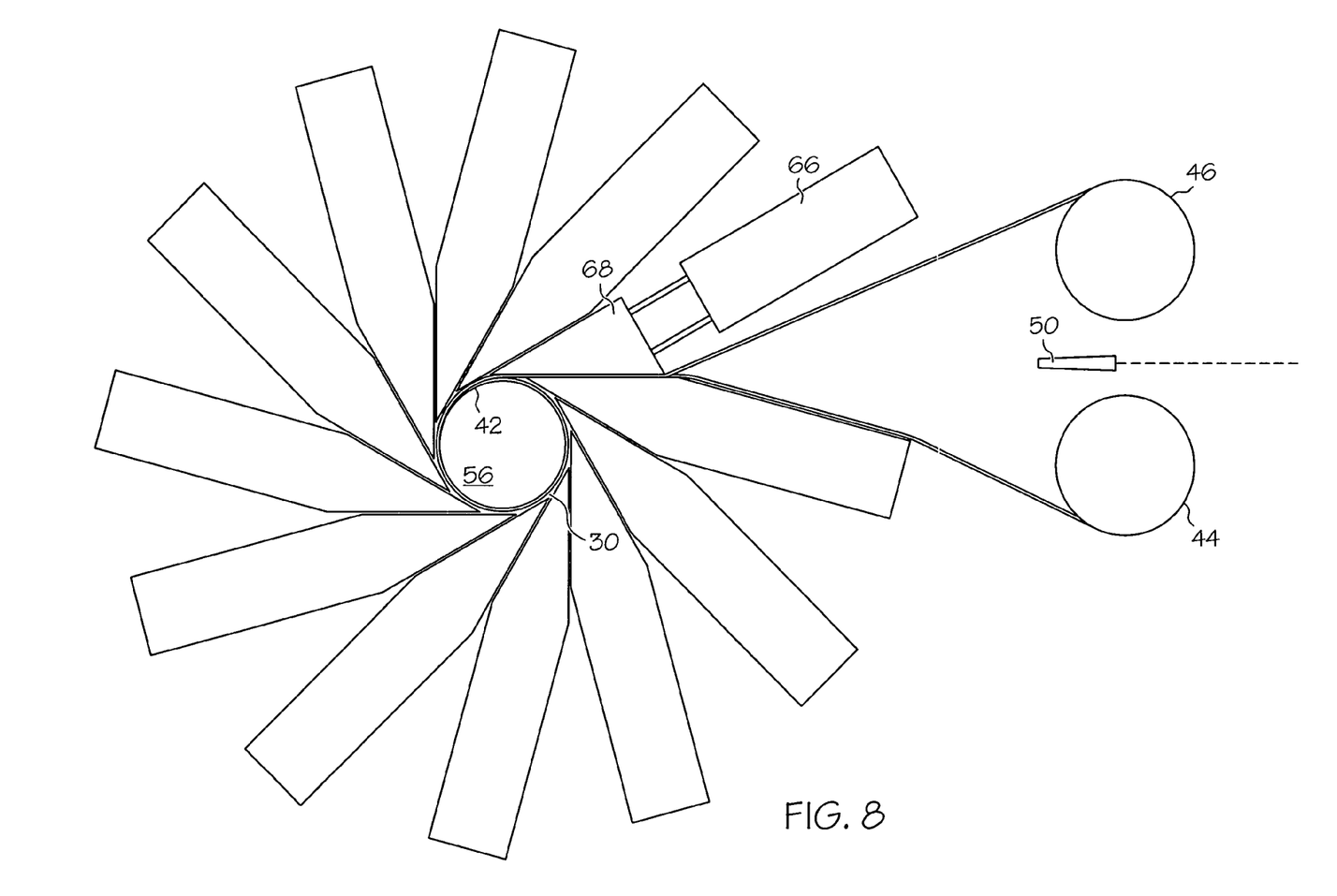
FIG. 8 shows an embodiment of the invention.

FIG. 8 shows the tip 68 in a crimping position, having been actuated from the temporarily removed position. When the tip 68 is in a crimping position, the gap 26 may be substantially closed. Actuation of the tip 68 with respect to the body section 66 may be accomplished by any suitable method, such as an electromagnet, an actuator, a spring, etc. FIG. 8 also shows a portion of the sheet 42 loaded into the chamber 30 and forming a cavity 56.

Figure 9:
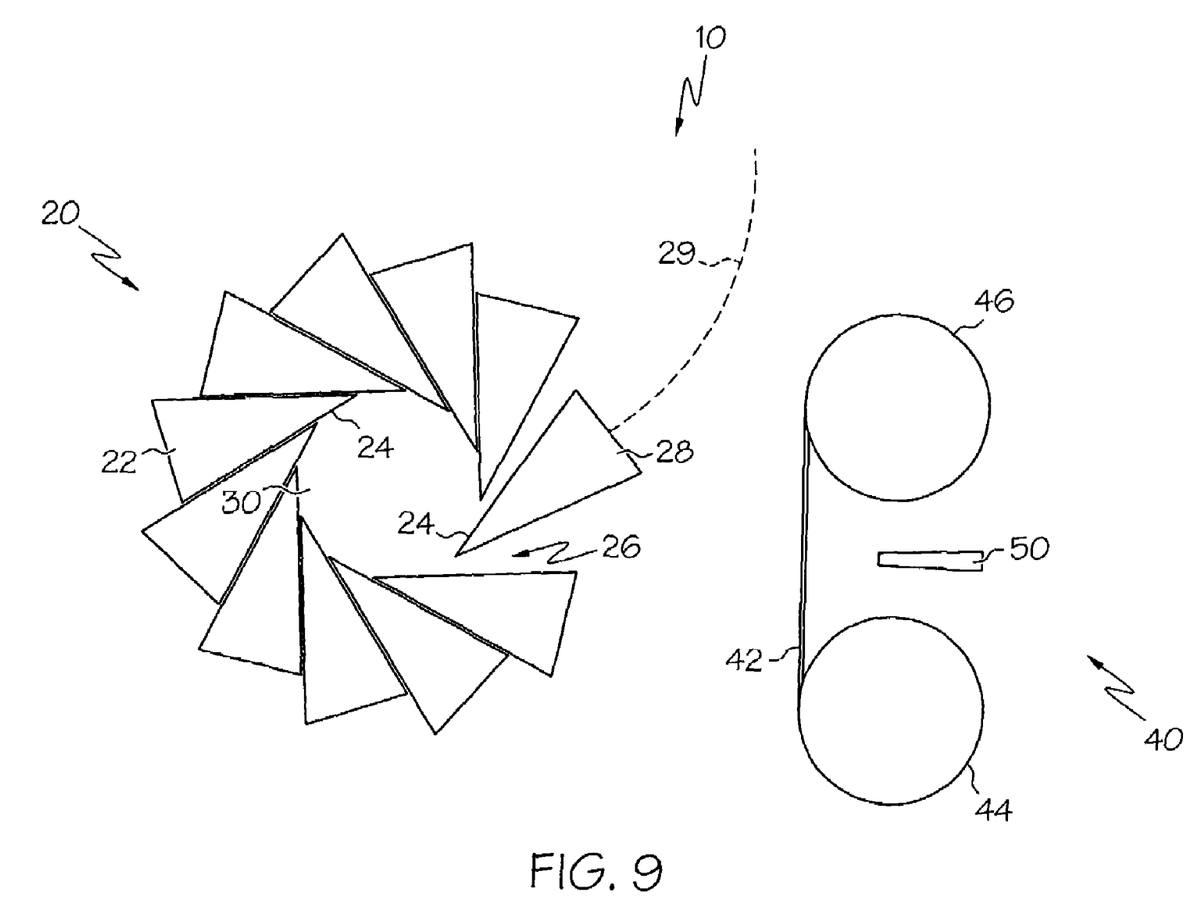
FIG. 9 shows another embodiment of the invention.

FIG. 9 shows another embodiment of a crimping apparatus 10, wherein a removable blade 28 may have a larger contacting surface 24 or a greater amount of surface area exposed in the chamber 30 than other blades 22 of the device. During a crimping process, the removable blade 28 may follow a unique crimping movement path. As the blades 22, 28 are moved to reduce the size of the chamber 30, the non-removable blades 22 may all follow similarly shaped crimping movement paths. A removable blade 28 may follow a unique crimping movement path, which may be non-symmetrical when compared to the crimping movement path of another blade 22.

A removable blade 28 which follows a non-symmetrical crimping movement path may further be moved by a movement mechanism 29 to a temporarily removed position while a protective sheet 42 is loaded into the chamber 30. The non-symmetrical crimping movement path may allow the apparatus 10 to have a larger gap 26 while the removable blade is in the temporarily removed position, and to minimize the spacing between the removable blade 28 and adjacent blades 22 during the crimping step.

In some embodiments, a crimping section 20 may be provided with a gap 26 built into the design of the crimper. For example, blades 22 may be arranged such that a gap 26 or spacing exists between two adjacent blades sufficient for a loading mechanism 50 to load a portion of a sheet 42 into the crimping chamber 30. In such embodiments, it may be desirable to include a non-symmetrical blade. During a crimping process, a non-symmetrical blade may follow a unique crimping movement path, which may be non-symmetrical when compared to the crimping movement path of another blade 22 or all of the other blades 22 of the device. A non-symmetrical blade may allow the apparatus 10 to have a larger gap 26 when the chamber 30 is fully opened, and may minimize the spacing between a non-symmetrical blade and adjacent blades 22 as the size of the chamber 30 is reduced. In some embodiments, a non-symmetrical blade may have a larger contacting surface 24 or a greater amount of surface area exposed in the chamber 30 than other blades 22 of the device. In some embodiments, a non-symmetrical blade may have a different shape than other blades 22 of the apparatus 10.

Figure 10:
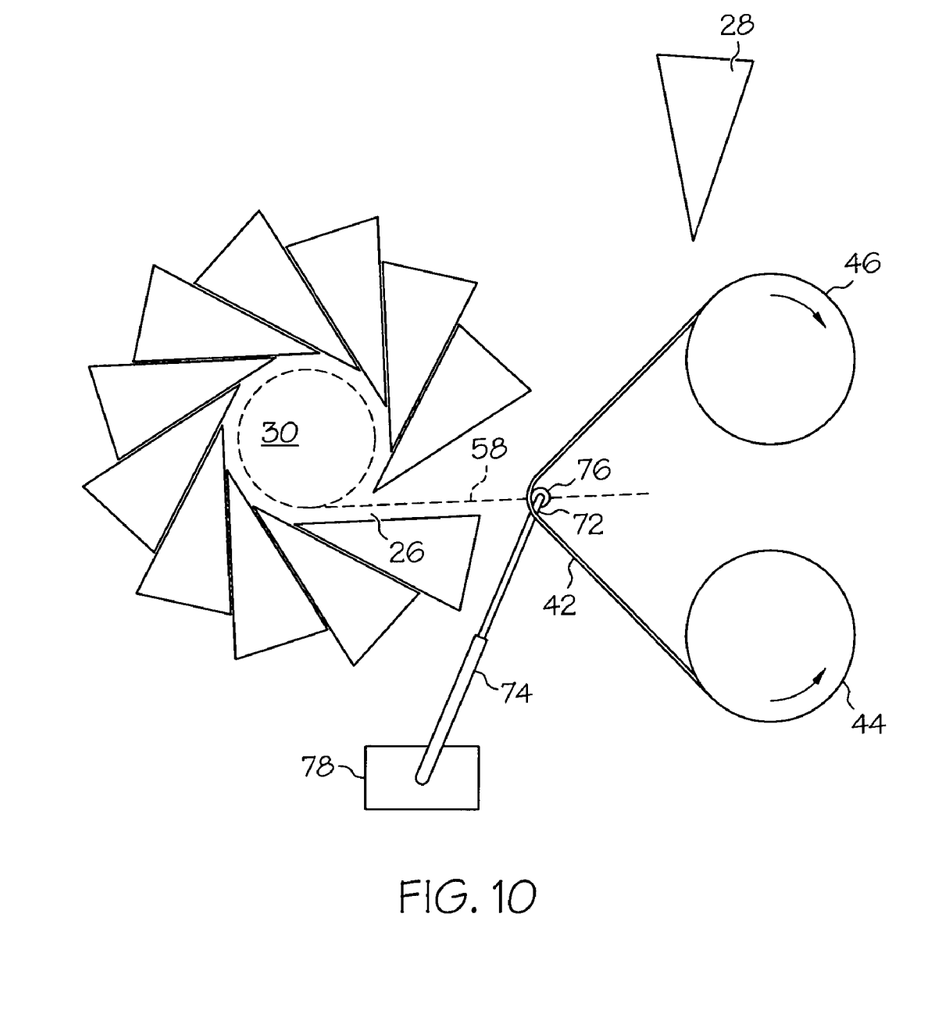
FIG. 10 shows another embodiment of the invention.

FIG. 10 shows another embodiment of a loading mechanism 50, which may include a cross-member 72 which desirably runs parallel to a longitudinal axis of the crimping chamber 30. In some embodiments, a cross-member 72 may be wire and may be supported at both ends. In some embodiments, a cross-member 72 may be an extension of a lever arm 74 or lever arms of the loading mechanism 50. The cross-member 72 may include a roller 76 to aid in placement of the sheet 42. The cross-member 72 may be moved along a travel path 58 which travels through the gap 26 and into the chamber 30. In some embodiments, the travel path 58 may travel about the periphery of the chamber 30. The cross-member 72 may be moved along the travel path 58 by a control device 78, which may include a lever arm 74 which may be extendable.

In some embodiments, an apparatus 10 may include a plurality of removable blades 28, which may allow for a larger gap 26. In some embodiments, when the removable blades 28 are in a temporarily removed position, a gap 26 may be large enough to load an uncrimped stent into the chamber 30 laterally through the gap 26. In such embodiments, a loading mechanism 50 may load both a stent and the protective sheet 42 into the chamber 30 simultaneously. For example, a loading mechanism 50 may contact and move a stent laterally toward the gap 26. The stent may contact the sheet 42 and may push a portion of the sheet 42 through the gap 26 and into the chamber 30 as the stent is moved through the gap 26 and into the chamber 30.

Figure 11:
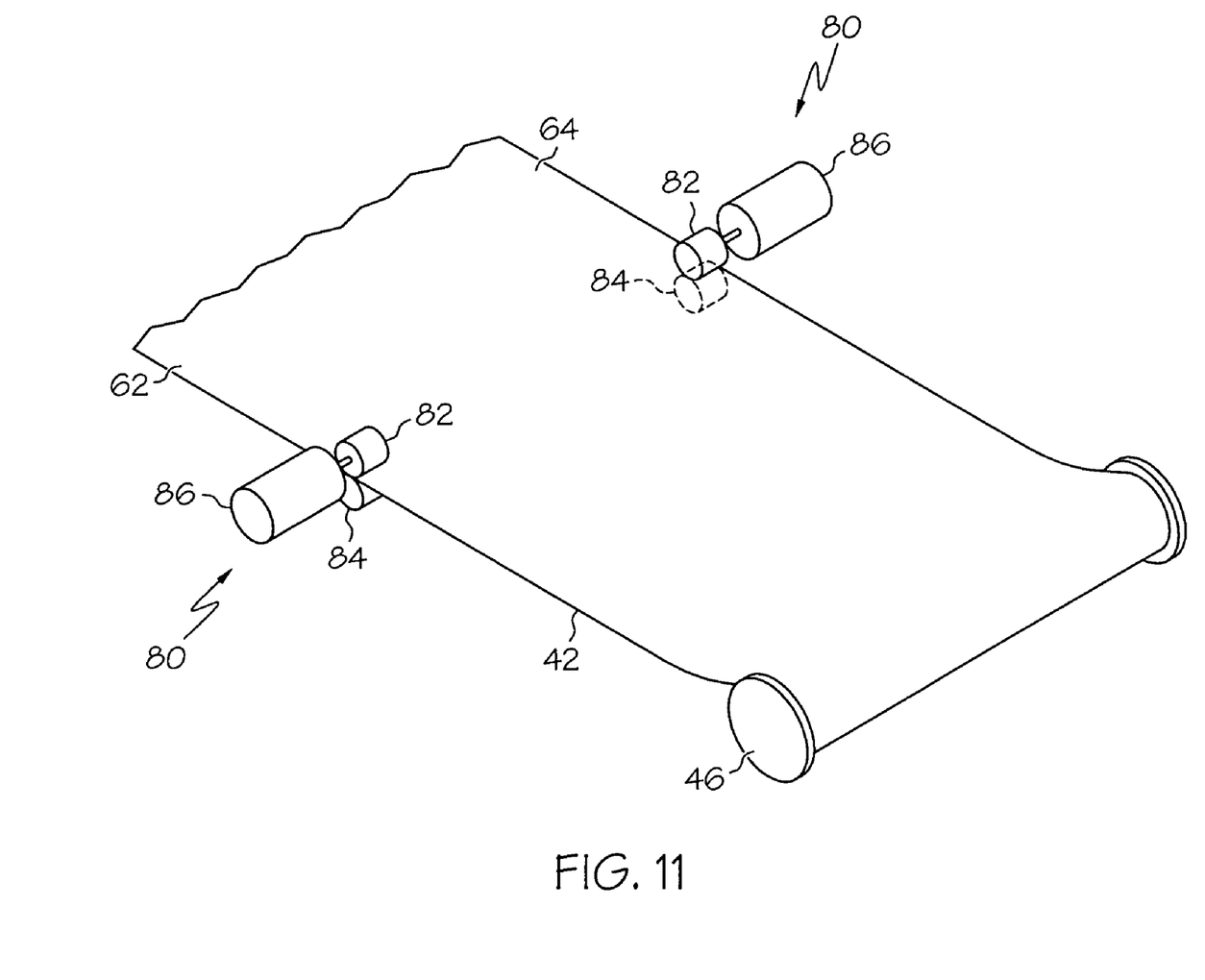
FIG. 11 shows a portion of an embodiment of the invention.

FIG. 11 shows an embodiment of a tension device 80 to control the tension of the sheet 42. When it is desired to use a system other than the supply roller 44 and/or the discard roller 46 to control the tension of the sheet 42, one or more separate tension devices 80 may be provided. Desirably, tension devices 80 may be arranged to engage the sheet 42 between the supply roller 44 and the chamber 30, and/or between the chamber 30 and the discard roller 46. Tension devices 80 may comprise any mechanism suitable for engaging the sheet 42 and applying a directional force to the sheet 42. In one embodiment, a tension device 80 may comprise a motor 86 arranged to drive a driven roller 82. A passive roller 84 may be arranged to engage the sheet 42 in conjunction with the driven roller 82. In some embodiments, the driven roller 82 and/or passive roller 84 may be moved away from one another to release the sheet 42 when desired. Tension devices 80 may apply forces to the sheet 42 which act to remove the sheet 42 from the chamber 30.

In some embodiments, the crimping apparatus 10 may be used to crimp tapered medical devices, which may be tapered along their entire length or a portion or portions thereof. The crimping section 20 may be configured to have a tapered or shaped crimping chamber according to the principles disclosed in U.S. patent application Ser. No. 10/788,088 or any other suitable device for crimping a tapered article.

A tapered medical device generally includes a first region having a first diameter and a second region having a second diameter of different size. A taper may extend along the entire length or along less than the entire length of the medical device. A taper may begin or end at an end of the medical device or elsewhere along the length of the medical device. This size disparity may exist in the crimped and/or uncrimped configurations. When crimping a tapered medical device using various embodiments of the crimping apparatus 10, it may be desirable to remove a greater portion of length of the sheet 42 on a first side 62 of the sheet than of a second side 64 of the sheet during crimping. Tension devices 80 may be configured to pull a greater length of the first side 62 of the sheet than the second side 64 during a crimping operation. While applying tension to the sheet 42 during a crimping operation, tension devices 80 may remove any excess portion of the sheet 42 that is no longer needed to surround the medical device. Thus, tension devices 80 may remove appropriate portions of the sheet 42 during a crimping operation when crimping a tapered medical device.

In various embodiments, the invention may be used as a stand alone system for crimping/loading a stent upon a delivery catheter, or may be used in conjunction with other steps and/or devices in a multiple step crimping/loading system.

In some embodiments, the invention may comprise the protective sheet loader section 40 (see FIG. 1) as herein described. An inventive protective sheet loader section 40 may be used with any suitable crimping device which may receive a portion of the sheet 42 within the crimping chamber.

The invention is also drawn to methods of reducing the size of a medical device using a protective sheet 42 as herein described. For example, a method of reducing the size of a medical device may comprise providing an apparatus for reducing the size of a medical device, such as a crimper. Desirably, the apparatus includes a crimping chamber, wherein the size of the chamber is adjustable. A sheet of material may be provided and a portion of the sheet of material may be disposed within the chamber. A medical device may be provided, and the medical device may be disposed within the chamber such that the first portion of the sheet of material within the chamber is oriented about the medical device. The size of the chamber may be reduced to reduce the size of the medical device. Desirably, the sheet of material may be kept in tension, and any excess portion of the sheet may be removed from the chamber as the size of the chamber is reduced.

In some embodiments, a medical device which may be reduced in size may be a stent, whether self-expanding, balloon expandable or a combination of the two, a graft, a stent-graft or another expandable framework regardless of whether it is capable of supporting a vessel.

In some embodiments, the invention may be directed to the following numbered paragraphs:

1. A protective sheet loader for use with a stent crimper comprising:
   a supply roller;
   a discard roller;
   a sheet of material spanning between the supply roller and the discard roller; and
   a loading mechanism constructed and arranged to load a portion of the sheet of material into the crimping chamber of a stent crimper.

2. The protective sheet loader of paragraph 1, wherein the sheet of material comprises PTFE.

3. The protective sheet loader of paragraph 1, wherein the loading mechanism comprises a source for providing a stream of gas.

4. The protective sheet loader of paragraph 3, wherein the gas is air.

5. The protective sheet loader of paragraph 3, wherein the gas is nitrogen.

6. A method for loading a crimping device having a chamber comprising the steps of:
   1) providing a source of material; 2) directing a flow of gas at the material to force at least a portion of the material into the chamber.

7. The method of paragraph 6, wherein the material comprises a sheet.

8. The method of paragraph 6, wherein the material comprises PTFE.

9. A method of crimping a stent comprising:
   providing a stent crimper;
   providing a sheet of protective material;
   disposing a stent and at least a portion of the sheet of protective material within the stent crimper such that the portion of the sheet of protective material forms a barrier between the stent and the stent crimper;
   crimping the stent using the stent crimper such that the stent crimper does not directly contact the stent.

10. The method of paragraph 9, wherein the stent crimper directly contacts the sheet of protective material, and the sheet of protective material directly contacts the stent during the crimping step.

11. The method of paragraph 9, further comprising removing the stent and the portion of the sheet within the stent crimper from the stent crimper.

12. The method of paragraph 11, further comprising disposing a second stent and a second portion of the sheet of protective material within the stent crimper such that the second portion of the sheet of protective material forms a barrier between the second stent and the stent crimper; and performing a second crimping step comprising crimping the second stent using the stent crimper such that the stent crimper does not directly contact the second stent.

13. The method of paragraph 12, wherein the stent crimper directly contacts the second portion of the sheet of protective material, and the second portion of the sheet of protective material directly contacts the second stent during the second crimping step.

14. The method of paragraph 9, wherein the stent comprises a coating.

15. The method of paragraph 14, wherein the coating comprises a drug.

The above disclosure is intended to be illustrative and not exhaustive. This description will suggest many variations and alternatives to one of ordinary skill in this field of art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

The invention claimed is:

1. An apparatus for reducing the size of a medical device comprising:
   a crimping device comprising a plurality of moveable blades arranged to form a chamber, the size of the chamber being adjustable;
   a first roller, a second roller and a sheet of protective material spanning between the first roller and the second roller; and
   a loading mechanism arranged to load a portion of the sheet of protective material into the chamber.

2. The apparatus of claim 1, wherein the loading mechanism comprises a cross-member that actuates along a travel path.

3. The apparatus of claim 1, wherein the loading mechanism comprises a source for providing a stream of gas.

4. The apparatus of claim 3, wherein the source for providing a stream of gas comprises a gas jet.

5. The apparatus of claim 4, wherein the gas jet directs gas pressure against a portion of the sheet of protective material which is oriented within the chamber.

6. The apparatus of claim 5, wherein the gas pressure causes the portion of the sheet of protective material which is oriented within the chamber to abut an internal periphery of the chamber.

7. The apparatus of claim 1, wherein the loading mechanism is arranged to move on a track.

8. The apparatus of claim 1, wherein the sheet of protective material comprises PTFE.

9. The apparatus of claim 1, wherein the sheet of protective material has a coefficient of friction of 0.1 or less.

10. The apparatus of claim 1, wherein the first roller and the second roller are configured to apply tension to the sheet of protective material.

11. The apparatus of claim 1, further comprising a removable blade which may be temporarily removed as the sheet of protective material is loaded into the chamber.

12. The apparatus of claim 1, wherein the first roller comprises a supply roller and the second roller comprises a discard roller.

13. A method comprising:
providing a crimping device for reducing the size of an expandable medical device, the crimping device having a chamber defined by a plurality of movable blades, the size of the chamber being adjustable;
providing a sheet of material;
providing an expandable medical device;
disposing a first portion of the sheet of material within the chamber;
disposing the expandable medical device within the chamber such that the first portion of the sheet of material within the chamber is oriented about the expandable medical device; and
reducing the size of the chamber by moving the blades sufficiently to reduce the size of the expandable medical device.

14. The method of claim 13, further comprising applying tension to the first portion of the sheet of material within the chamber while reducing the size of the chamber.

15. The method of claim 13, wherein disposing a first portion of the sheet of material within the chamber includes forcing the first portion of the sheet of material into the chamber using pressurized gas.

16. The method of claim 15, wherein the pressurized gas causes the first portion of the sheet of material to abut an inner periphery of the chamber.

17. The method of claim 13, wherein the sheet of material comprises PTFE.

18. The method of claim 13, further comprising removing the expandable medical device and removing the first portion of the sheet of material within the chamber.

19. The method of claim 18, further comprising disposing a second portion of the sheet of material within the chamber as the first portion is removed.

20. The method of claim 19, further comprising:
providing a second article expandable medical device;
disposing the second article expandable medical device within the chamber such that the second portion of the sheet of material within the chamber is oriented about the second expandable medical device; and
reducing the size of the chamber sufficiently to reduce the size of the second expandable medical device.

21. The method of claim 13, wherein the step of providing a sheet of material further comprises providing a first roller and a second roller, the sheet of material spanning between the first roller and the second roller.

22. The method of claim 13, wherein the expandable medical device is a stent.

23. A method of reducing the size of an article comprising:
providing a device for reducing the size of an article, the device having a chamber, the size of the chamber being adjustable;
providing a sheet of material;
providing an article;
forcing a first portion of the sheet of material into the chamber using pressurized gas;
disposing the article within the chamber such that the first portion of the sheet of material within the chamber is oriented about the article; and
reducing the size of the chamber sufficiently to reduce the size of the article.

24. The method of claim 23, wherein the pressurized gas causes the first portion of the sheet of material to abut an inner periphery of the chamber.

* * * * *